United States Patent [19]

Tanenbaum

[11] 4,395,615

[45] Jul. 26, 1983

[54] APPARATUS FOR WELDING METAL TRUSSES

[76] Inventor: Joseph M. Tanenbaum, 4 Dewbourne Ave., Toronto, Ontario, Canada, M5P 1Z2

[21] Appl. No.: 285,496

[22] Filed: Jul. 21, 1981

Related U.S. Application Data

[62] Division of Ser. No. 179,634, Aug. 20, 1980, abandoned.

[30] Foreign Application Priority Data

Aug. 15, 1980 [CA] Canada ................................ 358388

[51] Int. Cl.³ ............................................. B23K 11/32
[52] U.S. Cl. ...................................... 219/79; 219/56; 219/78.14; 219/111
[58] Field of Search ................... 219/56, 107, 79, 111, 219/58, 78.14

[56] References Cited

U.S. PATENT DOCUMENTS

| | | | |
|---|---|---|---|
| 1,707,405 | 4/1929 | Lunn | 219/78.14 |
| 2,429,186 | 10/1947 | Johnson | 219/111 |
| 3,158,731 | 11/1964 | Cape | 219/79 |
| 3,288,977 | 11/1966 | Keller | 219/79 |
| 3,899,653 | 8/1975 | Spinnato | 219/111 |
| 4,262,184 | 4/1981 | Cerutti | 219/58 |

OTHER PUBLICATIONS

Metals Handbook 8th edition, vol. 6, Welding and Brazing American Society of Metals, Metals Park, Ohio, 1971, p. 413.

Kruse "Electronic Controls for Resistance Winding Machine" in Siemen Review XLIV 1977, #2, pp. 76-80.

Primary Examiner—Elliot A. Goldberg
Attorney, Agent, or Firm—Weldon F. Green

[57] ABSTRACT

Apparatus for fabricating metal trusses having spaced preformed chord members of generally longitudinal predetermined length and cross-section joined by at least one preformed supporting web member of predetermined length and cross-section by electrically resistance welding together the chord and web member at a common region of contact with the chord member having a smaller cross-sectional area than the web member at the common region of contact. A device includes in to place a station for cleaning the chord and web members, means for moving the clean chord and web members to an assembly station for assembling the chord members in spaced relation joined by the web member. A device for passing the assembled truss along a support to the electrical resistance welder having opposed first and second electrodes of unequal resistance and adapted to releasably clamp the chord and web members respectively at the common region of contact. The welder has at least four pairs of approved electrodes to minimize distortion.

4 Claims, 16 Drawing Figures

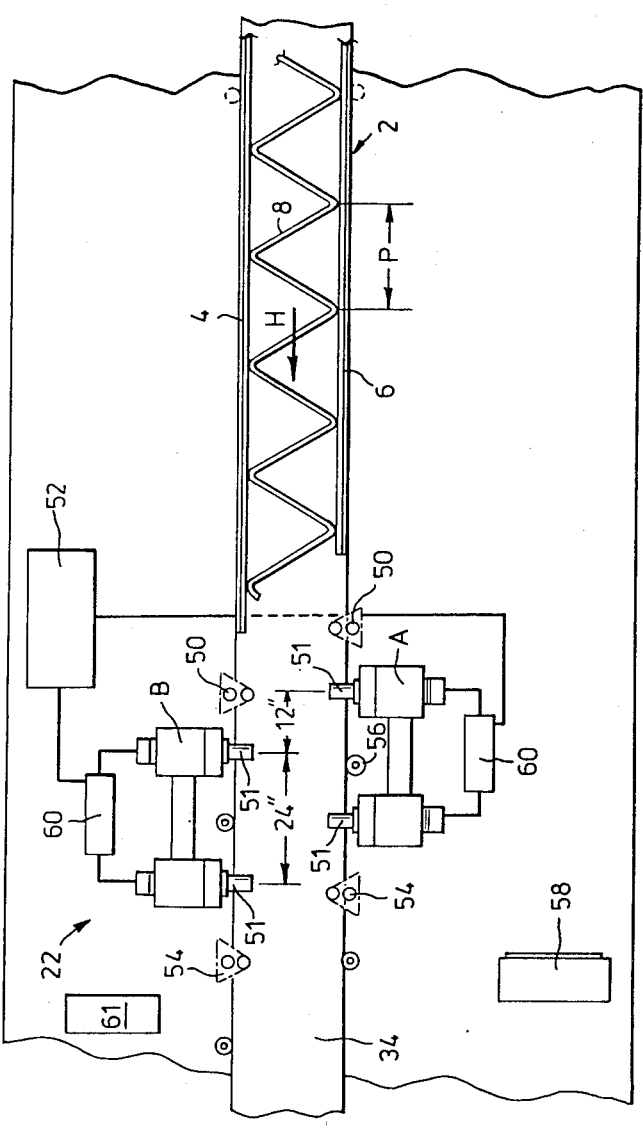
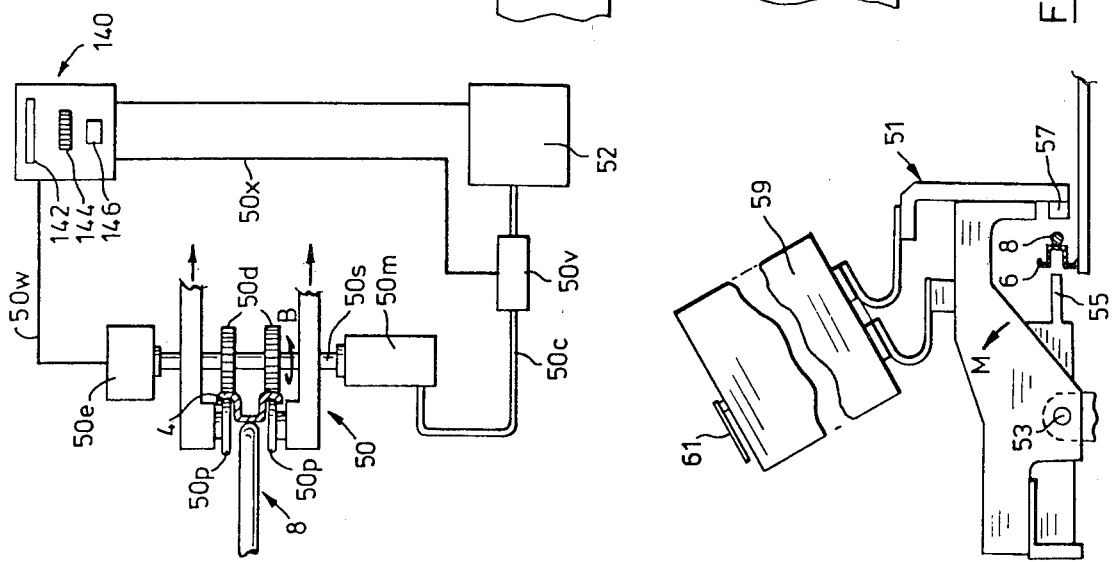

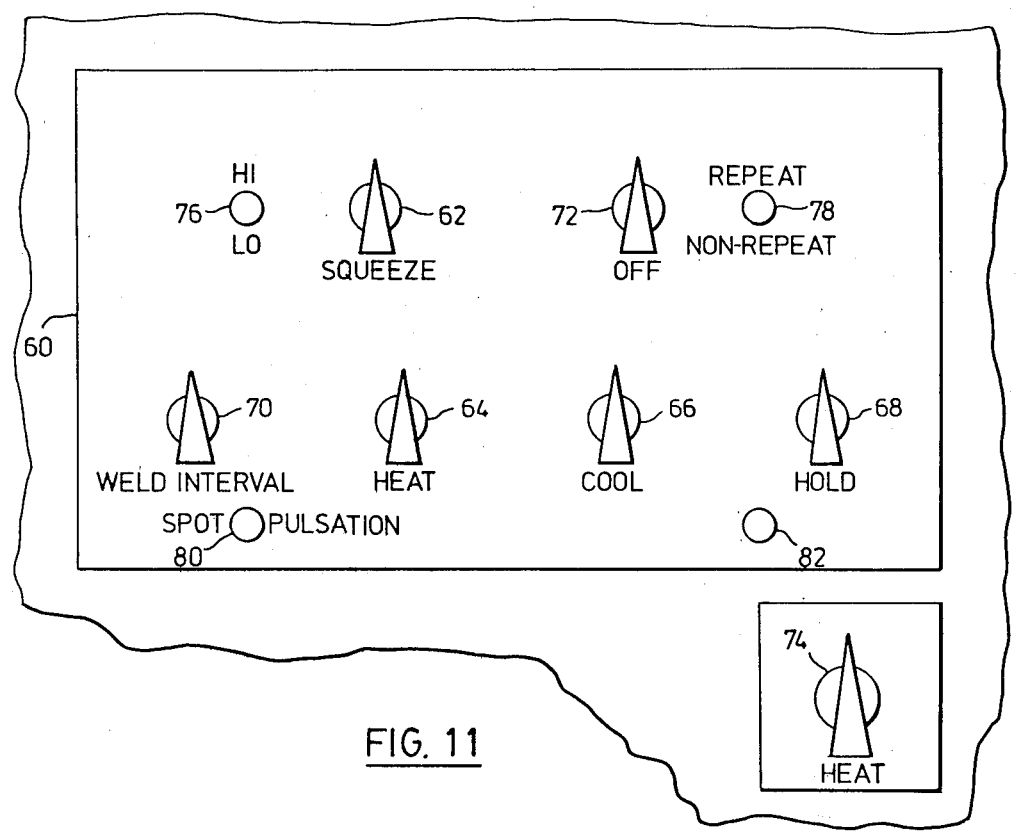
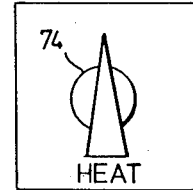
FIG. 11
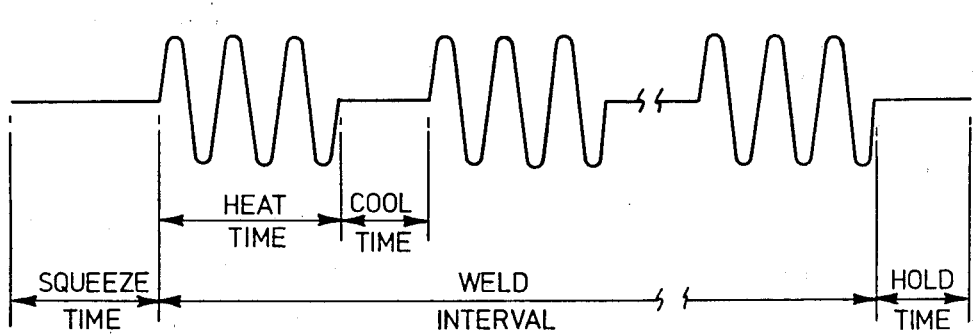
FIG. 12

APPARATUS FOR WELDING METAL TRUSSES

This is a division of application Ser. No. 179,634 filed Aug. 20, 1980 now abandoned.

FIELD OF THE INVENTION

This invention relates to improvements in a method for welding structural components together by fusion and particularly by means of a novel application of electrical resistance welding procedures.

More particularly, this invention relates to improvements in the fabrication of open web structural steel joists or trusses using the improved welding method and includes improvements in equipment for automatically implementing and controlling the sequential steps employed in fabricating the open web structures and in the testing of the adequacy of the welds.

BACKGROUND OF THE INVENTION

Joists or trusses include at least two chord or chord-like members connected by suitable load distributing lattices or webs. A typical joist or truss consists of two parallel chord members joined by an intermediate supporting web which may comprise a solid section or a pattern of struts designed to ensure that such structure has requisite load bearing capabilities.

A typical web of the type under consideration takes the form of a suitable structural steel rod bent upon itself into an undulating or zig-zag configuration of generally uniform pattern with the respective apices presented by the bent rod secured or connected to the spaced upper and lower chord members which members are usually arranged in parallel relation.

When such structure is fabricated out of steel and used to support the flooring or carry ceiling components it is commonly referred to as an "open-web" steel joist.

A typical method of attaching or connecting chord members to the web apices is by means of electrical resistance welding.

Electrical resistance welding is a process whereby fusion is produced by the heat generated from the resistance of the metal components to be joined together to the flow of electrical current when contacted and clamped between appropriate electrodes within an electrical circuit. No external heat source is required in order to achieve fusion, nor are any fluxes or filler materials necessary.

The current for resistance welding is normally supplied through a transformer which transforms the high voltage, low amperage power supply to usable high amperage current at low voltages. The pressure for the electrode clamping forces is generated by a suitable hydraulic system.

In any electrical conductor, current flow creates heat. The amount of heat (H) generated depends upon the amount of current (I), the resistance of the conductor (R) and the time (T) during which the current is flowing. Heat generated in resistance welding can be expressed in the following manner:

$$H = I^2 R T$$

H = heat generated in joules
I = current in rms amps
R = resistance of the work in ohms
T = time of current flow in seconds This formula indicates that the heat generated is directly proportional to the square of the welding current and to the resistance and to the time of current flow. The heat generated in such a procedure is used in part to fuse the chord and web members together in the regions of contact but with some of their useful heat being lost by conduction to the work pieces themselves and to the contacting clamping electrodes.

Radiation loss to the atmosphere is relatively insignificant.

The heat lost by conduction from the weld zone to the work pieces and to the contacting electrodes is directly proportional to the temperature differential existing between them. The greater the temperature differential therefore the greater the heat loss. This heat loss not only produces discoloration, warpage or twisting but undesirable metallurgical changes in the work pieces in the form of large grain growth in the region immediately surrounding the region of contact commonly designated the weld zone or the "nugget".

Large grain growth is undesirable because it produces weaknesses and brittleness at the weld joints and cause failure.

It follows that by controlling heat lost or dissipation by conduction, discoloration, warpage or twisting and large grain growth can be reduced. Further it is apparent that by lowering the temperature differential the greater will be the tendency to localize or confine the generated heat to the weld zone or "nugget", and therefore the escape of said generated heat energy from said region of contact will be minimized.

According to the formula, resistance is a critical factor in the generation of heat.

In making a weld, the current is passed from one electrode through the base metal in the work pieces to the other electrode. During this passage the current encounters several resistance zones including:
 (a) the electrical resistance of each electrode;
 (b) the contact resistance between each electrode and the base metal, the magnitude of which depends on the surface condition of the base metal and electrode, the size and contour of the electrode face, and the electrode clamping force;
 (c) the resistance of each piece of the base metal which is directly proportional to the resistivity of the base metal and its thickness and inversely proportional to the cross-sectional area of the current path;
 (d) the base metal interface where the weld formation starts, which is the point of highest resistance and therefore the point of greatest heat generation.

Should the surface of the base metal present oxides or scale then the resistance of the base metal would be correspondingly higher than if the base metal was free of same. Therefore the heat generated in the weld zone would be higher than normal and concomitantly the temperature differential between the weld zone and the surrounding metal would be greater than normal which results in undesirable grain growth as mentioned above. As well, the scale tends to impede the conduction of heat between the two work pieces being joined, and presents an unclean surface for welding which results in sparking during the welding operation and ultimately produces an unacceptable joint or connection. Accordingly, each work piece of base metal should be kept substantially free of scale.

Also, for best results the electrodes should be kept substantially free of the oxide coatings.

In making a satisfactory weld there is one factor not always given due consideration because of the difficulty in accurately predicting the precise effect. This factor is correct heat balance which is the condition in which the fusion zone in each work piece to be joined undergoes approximately the same degree of heating. The quality of the weld is enhanced when each work piece to be joined experiences the same degree of heating.

As mentioned above the resistance of each work piece is inter alia inversely proportional to the cross-sectional area of the current path. Therefore when resistance welding two equal cross-sectional areas of the same metal the heat balance is generally automatic. However, joists or trusses typically have disproportionate thicknesses or cross-sectional areas of chord members and web rods and therefore the heat balance is not automatic as the cross-sectional area in the common region of contact heat up at different rates. In welding dissimilar cross-sectional areas, a longer period of current flow or heat cycle is required to provide a more uniform distribution of heat throughout the asymmetrical resistance path extending between the clamping electrodes.

A number of pieces of equipment and proposals have heretofore been developed and used for welding the chord components of a joist or a truss to the web on an assembly line basis so as to reduce the cost of same. The quality however of the welds of the finished joists or trusses has also given some concern.

U.S. Pat. No. 3,158,731 discloses apparatus for automatically fabricating a truss where the chords are continuously formed in roller dies from coiled strip material while web wire also from a coil is straightened then bent into a zig-zag shape whereupon all three components are assembled together then resistance welded together and finally the truss so produced is automatically cut into lengths and painted.

Another alternative is illustrated in U.S. Pat. No. 3,288,977 which relates to a welding device which automatically moves the latticing strips in a step-by-step manner, with pauses between the motion for profiling the latticing into a zig-zag configuration and for welding the latticing to the chords. This patent further discloses testing equipment which comprises hydraulic cylinders and grippers which will apply a force F to one of the welded joints on the upper chord, while a force F/2 is applied to each of the adjacent two welded joints on the lower chord.

Still another alternative is disclosed by U.S. Pat. No. 3,427,699 which relates to a production line operation wherein chords of predetermined cross-section are stacked at two separate stations and in parallel relation and individually fed forward from the bottom of the stack, then sheared to length and aligned with a web of zig-zag configuration. The chords and web are then fed forwardly together in continuous alignment and welded together.

A further alternative is illustrated in U.S. Pat. No. 3,487,861 which discloses apparatus providing means for performing the steps of simultaneously supplying a pair of straight side wires and an intermediate straight wire from several sources, in side-by-side relation in one direction along a path bending the intermediate wire into zig-zag form while driven along such path and then welding the apices to the flanking side wires to complete the truss structure.

Still another arrangement is found in U.S. Pat. No. 3,641,303 which illustrates a method and apparatus for continuously producing a truss element in successive unit lengths by shaping an extended length of suitable strip material to present a zig-zag configuration, while in a position adjacent a chord members provided with integral ribs formed thereon, then welding the web and chord together. Each chord presents ribs of relatively small cross-sectional area which flow under the force and heat generated by the clamping electrodes of a suitable resistance welding machine, and thereby form the welds which join the web to the chord member.

OBJECTS OF THE INVENTION

The principal object of this invention is to provide improvements in the electrical resistance method of welding structural steel members or the like, wherein electrodes are clamped over the members in the region of the weld zone and electrical energy applied thereto; and, more particularly, to provide a welded joint of greater quality and strength.

More particularly, it is an object to provide an improved method for controlling the application of electrical energy to the work pieces whereby the useful heat generated by the current and the resistivity of the work pieces is more finitely localized in the weld zone itself and without appreciable heat loss by conduction of heat away from the weld zone to the more remote regions of the work pieces.

Still another object of this invention is to provide an improved method as indicated in which the heat generated by impressing an electrical current through the abutting work pieces and within the weld zone is more uniformly distributed within each work piece.

Still another very important object resides in providing an improved electrical resistance welding method that can be adapted to substantially balance the generation of heat within each abutting work piece in the region of the weld zone, over a wide range of work piece sizes.

A further object of this invention is to provide for an improved method as described for fabricating trusses, and more particularly to the fabrication of open-web steel joists having improved load bearing capabilities.

Yet another object resides in providing for an improved method for fabricating open-web steel joists wherein the quality and strength of each welded joint therein is substantially the same.

It is also an object of this invention to provide a safer method for electrically resistance welding structural steel members wherein sparking at the weld zone during welding is substantially reduced.

A further important object resides in providing an improved method as indicated which is susceptible of implementation and control through automated equipment for the most part in order to relieve the electrical resistance welding machine operator from the demands of constant supervision.

Still another very important object resides in providing apparatus for controlling the improved electrical resistance method for welding structural steel members or the like, and more particularly to equipment control devices for automatically controlling the fusion of the abutting work pieces in the weld zone.

Another object of this invention resides in providing equipment for substantially automating the fabrication of structural steel members such as open-web steel joists in order to increase the rate of production and decrease the cost of manufacture of same.

It is also an object of this invention to utilize electrodes having longer effective wear characteristics in order to substantially reduce the frequency of replacing same.

It is yet another object of this invention to provide improvements in equipment for testing the adequacy of the welds fabricated in accordance with this invention.

FEATURES OF THE INVENTION

The principal feature of this invention resides in providing a welding process for joining structural members together along a common region of contact by means of fusion through the application of heat generating electrical energy to the common region of contact, and more particularly for applying to said region of contact several timed controlled impulses of the heat generating electrical energy in sufficient strength adapted to incrementally raise the temperature of said members in said region contact in stages so as to minimize the escape of generated heat energy from the region of contact and effectively weld the members along said common region of contact and substantially reduce the formation of weld defects in the region of contact.

The temperature of each member in the region of contact is substantially the same during the application of heat generating electrical energy. The strength of each impulse of electrical energy is also substantially the same; and as well the time duration of each impulse of electrical energy is substantially the same.

More particularly, it is a feature to provide a method for welding metallic members having predetermined cross-sectional areas whereby the metallic members are positioned and clamped so as to present at least one region of contact and then applying to said region of contact several controlled impulses of electrical energy in sufficient strength so as to localize the generation of heat energy in the region of contact and uniformly heat and incrementally raise the temperature of said members in said region of contact in stages for effectively welding said metallic members along said region of contact and substantially reduce the formation of metallurgical defects in said region of contact. The strength of each successive impulse of electrical energy will depend on the cross-sectional area of the members in the region of contact.

More particularly, it is a feature to provide a method for welding structural members along their common region of contact by applying, for a selected timed interval, a controlled electric current having sufficient strength so as to generate heat in the members in the region of contact during the selected timed interval and then interrupting the application of electric current for a selected timed interval immediately upon the elapse of said first preceding timed interval so as to interrupt the generation of heat in the region of contact during the selected timed interval of interrupting the electric current; and then repeating the application of electric current and the interruption of electric current for said selected timed intervals respectively, successively, several times, immediately upon the elapse of the preceding timed interval of interrupting the application of electric energy, so as to uniformly heat and incrementally raise the temperature of the members in the region of contact in stages and effectively weld the members along said common region of contact.

It has been empirically determined that for a certain specified range of materials having certain specified cross-sectional areas tabulated in tables 1 and 2, that the optimum time duration of each application of electric current is in the order of 0.45 seconds and that the optimum time duration of each interruption of application of electric current is in the order of 0.05 seconds. Moreover, effective results have been achieved by repeating the application and interruption of electric current between four and six times. The method outlined above achieves its maximum efficiency when the strength of each electric current during each of the several interruption steps is substantially zero.

Still another feature resides in applying the welding process as outlined to the fabrication of metal trusses having spaced chord members of generally longitudinal predetermined length and cross-section joined by at least one supporting member of predetermined length and cross-section. The cross-sectional area of the chord members in the region of contact is substantially smaller than the cross-sectional area of the web member in the region of contact. By applying a series of time controlled intermittent impulses of electric current to the common regions of contact the temperature of said members in the region of contact is incrementally raised in stages so as to minimize the temperature differential between the temperature of said members in said region of contact and the body of said members and thereby minimize heat loss by conduction and so minimize discolouration, warpage, twisting, and undesirable metallurgical changes in said members in the form of large grain growth in the region immediately surrounding the region of contact. The application of several time controlled intermittent impulses of electric current to the said region of contact is also adapted to uniformly heat said members in said region of contact so as to more evenly balance the distribution of heat in said members in said region of contact and enhance the quality of weld in said region of contact.

Still more particularly, is a feature of this invention to apply the novel application of electrical resistance welding procedures as outlined to the fabrication of open web steel joists having two spaced substantially parallel chord members joined together by a planar web bent into a substantially uniform undulating configuration between the parallel chord members so as to present a series of alternating opposite apices at the bends adapted to contact one of the spaced chord members respectively along regularly spaced intervals longitudinally of the chord members by welding the web member to the chord members at the common regions of contact.

The chord members used in the fabrication of open web steel joists are formed by drawing chord forming material through a chord forming station or machine for straightening, shaping, and then cutting the chord forming material at selected intervals.

The web member used in the fabrication of open web steel joists is formed at a web forming station or machine which uniformly bends equal sections of a web forming material into an undulating configuration of generally uniform pattern having a series of apices presented by the bent web forming material.

It is another feature of this invention to provide a method for automating the fabrication of open web steel joists as described by clamping at least one of the apices of the web member to one of the chord members and then applying thereto a series of time controlled intermittent impulses of electric current adapted to incrementally raise the temperature of the chord and web members in the region of contact in stages so as to minimize the escape of generated heat by conduction from said region of contact, and to uniformly heat said members in said region of contact so as to balance the distribution of heat therein and thereby effectively weld said members along said region of contact so as to substantially reduce the formation of weld defects in the region of contact. The members are then unclamped and the open web steel joist is fed along a welding path for a predetermined distance in a direction so as to present the next following apices for welding to the chord members. The clamping, application, and feeding steps are automatically repeated successively, several times, immediately upon the completion of the preceding feeding step so as to progressively weld each of the next following alternating opposite apices presented by the bent web member to the chord member respectively.

It is a feature of this invention that four adjacent apices presented by the web member are simultaneously and automatically welded during each of the several number of repetitions outlined above where two of the adjacent apices are welded to one of the chord members and the other two opposite adjacent apices are welded to the other chord member.

A further feature of this invention resides in a method for fabricating open web steel joists where the joist is fed along the welding path a distance equal to twice the regularly spaced interval between the common regions of contact along each of the chord members during each of the several number of repetitions of feeding as disclosed earlier.

It is a further feature of this invention to clean the surface of the chord and web members at a surface cleaning station, or wheelabrator, prior to welding said members so as to minimize sparking at said common regions of contact during welding and so as to maximize the weld strength of said joist at said common regions of contact.

Another feature of this invention resides in providing an electrical resistance welding machine for controlling the steps of said method, that include electrodes adapted to releasable contact and clamp the members together and transmit and apply the electrical energy to the member in said region of contact on an intermittent basis; a transformer associated with the electrodes for supplying the electrical energy, to be intermittently applied to the members in said region of contact; and a control device for controlling the intermittent application of electrical energy to the region of contact for a selected timed interval. The control device is capable of interrupting the application of electric energy for a selected timed interval so as to present a series of intermittent impulses of electric energy adapted to incrementally raise the temperature of the members in the region of contact in stages so as to minimize the escape of heat energy from said members in the region of contact and so as to balance the distribution of heat in said members in said region of contact and thereby effectively weld the members together at the region of contact.

The control device also includes a first timing device for activating the application of the several impulses of electric energy for a limited time period at preset selected timed intervals and a second timing device for activating the interruption of electrical energy for a limited period at preset selected timed intervals.

The electric resistance welding machine includes a pair of electrodes adapted to clamp the members together in said region of contact during welding. The electrodes include heat exchange means for cooling the electrodes during welding. As the heat exchange means also have a tendency to cool the members by conduction, and particularly cool the member having relatively small cross-sectional area, it is a further feature of this invention to provide two electrodes where one of said electrodes is of a material having relatively high electrical resistance to the transmission of electrical energy and adapted to contact the member having relatively small cross-sectional area, and where the second electrode is of a material having relatively low electrical resistance to the transmission of electrical energy and adapted to contact the member having relatively large cross-sectional area. The materials of said electrodes have been chosen so as to increase the effective life of the first and second electrode during the intermittent application of electrical energy to the members in the region of contact.

It is another feature of this invention to provide a first electrode having a tungsten copper beryllium composition and a second electrode having a copper beryllium composition.

More particularly it is a further feature of this invention to provide a first electrode of copper having a 10W3 designation and a second electrode comprised of copper having a RWMA Class 3 designation.

Another feature of this invention resides providing in a first electrode of a material adapted to inhibit the cooling of said member having relatively small cross-sectional area by said heat exchange means.

Another feature of this invention resides in providing apparatus for fabricating metal trusses having spaced preformed chord members of generally longitudinal predetermined length and cross-section joined by at least one preformed supporting web member of predetermined length and cross-section which are joined together at a welding station adapted to weld the spaced chord member to the web member at the common regions of contact. The chord members have relatively small cross-sectional area in said region of contact and the web member has a relatively large cross-sectional area at the common region of contact.

More particularly in the preferred embodiment the apparatus for fabricating metal trusses includes four pairs of first and second electrodes for simultaneously welding two adjacent apices presented by the web member to one of the chord members, and the other two opposite adjacent apices presented by the web member to said other chord member, whereby two pairs of said electrodes are located on one side of a conveyor belt and the other two pairs of electrodes are located on the other side of said conveyor belt.

It is yet another feature of this invention to provide a device for non-destructively simultaneously testing the shear strength of at least four welded joints presented by the metallic truss having two spaced substantially parallel chord members joined together by a substantially planar web member bent into a substantially uniform undulating configuration between the chord members so as to present a series of alternating opposite apices at the bends welded to the spaced chord members respectively along regularly spaced intervals longitudinally of the chord members; said device including; a clamping device for simultaneously clamping the chord members in at least four positions adjacent the welded joints, where said clamping device includes a device for eliminating the twisting of said welded joints from the plane defined by the web member during said simultaneous clamping; and a device for simultaneously applying a substantially perpendicular force relative said plane defined by the web member, to at least four of said apices defined by the bent web so as to test the shear strength of at least four of said welded joints.

These and other objects and features will become apparent in the following description to be read in conjunction with the sheet of drawings and tables.

DRAWINGS

FIG. 9 is a top plan view of the electrical resistance welding station.

FIG. 9a is a partial view illustrating the indexing mechanism.

FIG. 10 is a partial view illustrating side elevational view of each welding gun.

FIG. 11 is a partial view of the control panel of the welding sequence controller.

FIG. 12 is a graphic illustration of the application of several intermittent impulses of electric current applied to the chord and web member in the region of contact.

TABLES

Figure 1:
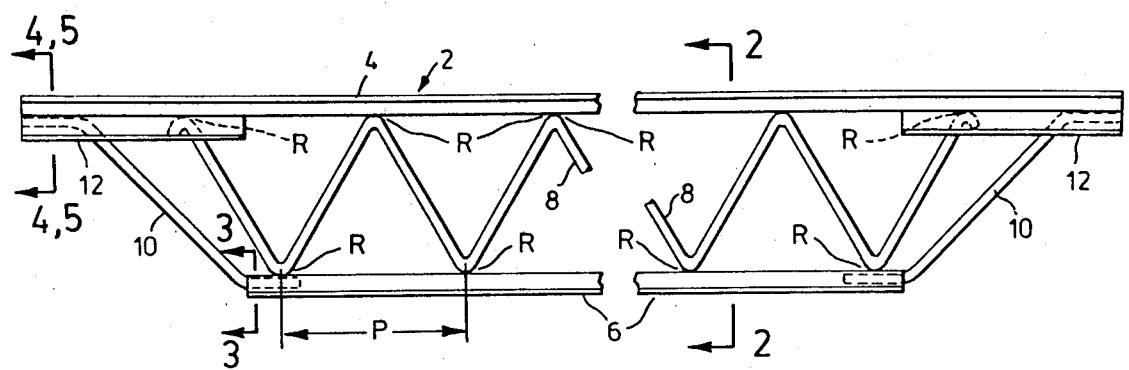
FIG. 1 is a partial side elevational view of the open web steel joist.

Table 1 tabulates the design shear strength times 2.5 and times 1.65 for various sizes of web and chord members.

Table 2 tabulates the optimum parameter settings for the application of several intermittent impulses of electric current applied to the chord and web members at the common region of contact.

DESCRIPTION OF THE PREFERRED EMBODIMENT OPEN WEB STEEL JOIST

Referring to the drawings and particularly to FIGS. 1, 2, 3, 4 and 5, the open web steel joist generally indicated at 2 consists of spaced parallel cold formed upper and lower chord members 4 and 6 respectively, which are resistance welded at panel points R to a continuous zig-zag web rod 8 so as to present an open web. The panel points R are located at the common regions of contact between the chord members 4 and 6 respectively and the apices presented by web member 8, and are equally spaced apart a distance known as the panel length P, which in the preferred embodiment is 24 inches.

Figure 2:
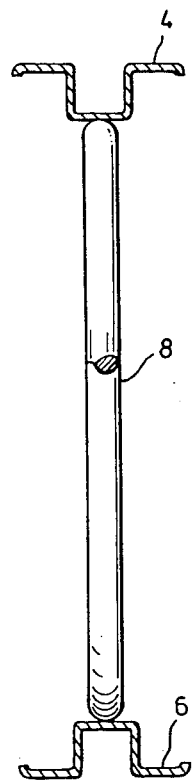
FIG. 2 is a cross-sectional view of the open web steel joist taken along the lines 2—2 in FIG. 1 revealing the cross-sectional configuration and areas of upper and lower chord members and web member.
Figure 3:
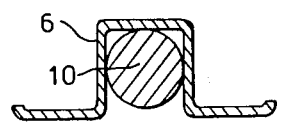
FIG. 3 is a cross-sectional view of the open web steel joist taken along the lines 3—3 in FIG. 1 revealing the lower chord member and end diagonal.

The upper chord member 4 and the lower chord member 6 have a generally channel shaped cross-section and are inversely disposed with reference to each other as best illustrated in FIG. 2. The web rod 8 has a circular cross-section. The cross-sectional area of the chord members 4 and 6 is different from the cross-section of the web rod 8 in the common region of contact, namely at panel points R.

Figure 4:
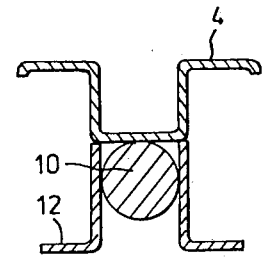
FIG. 4 is a cross-sectional view of the open web steel joist taken along the lines 4—4 in FIG. 1 revealing the upper chord member, end diagonal, and shoe.
Figure 5:
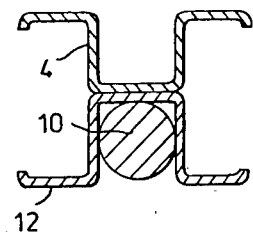
FIG. 5 is a cross-sectional view of the open web steel joist taken along the lines 5—5 in FIG. 1 and is an alternative to FIG. 4.

The ends of the open web steel joist present end diagonals 10 and shoes 12 which are arc welded to the joist 2 as shown in FIGS. 1, 3, 4 and 5. The shoes 12 may be formed from two L-shaped brackets as illustrated in FIG. 4 or alternatively may be generally channel-shaped as illustrated in FIG. 5. End diagonals 10 and shoes 12 and the arc welding of same to joist 2 do not form part of the invention but have been disclosed for completeness.

Upper chord member 4, lower chord member 6, zig-zag web rod 8, and diagonal 10, and shoes 12 are all fabricated from steel.

FORMATION OF CHORDS

Figure 6:
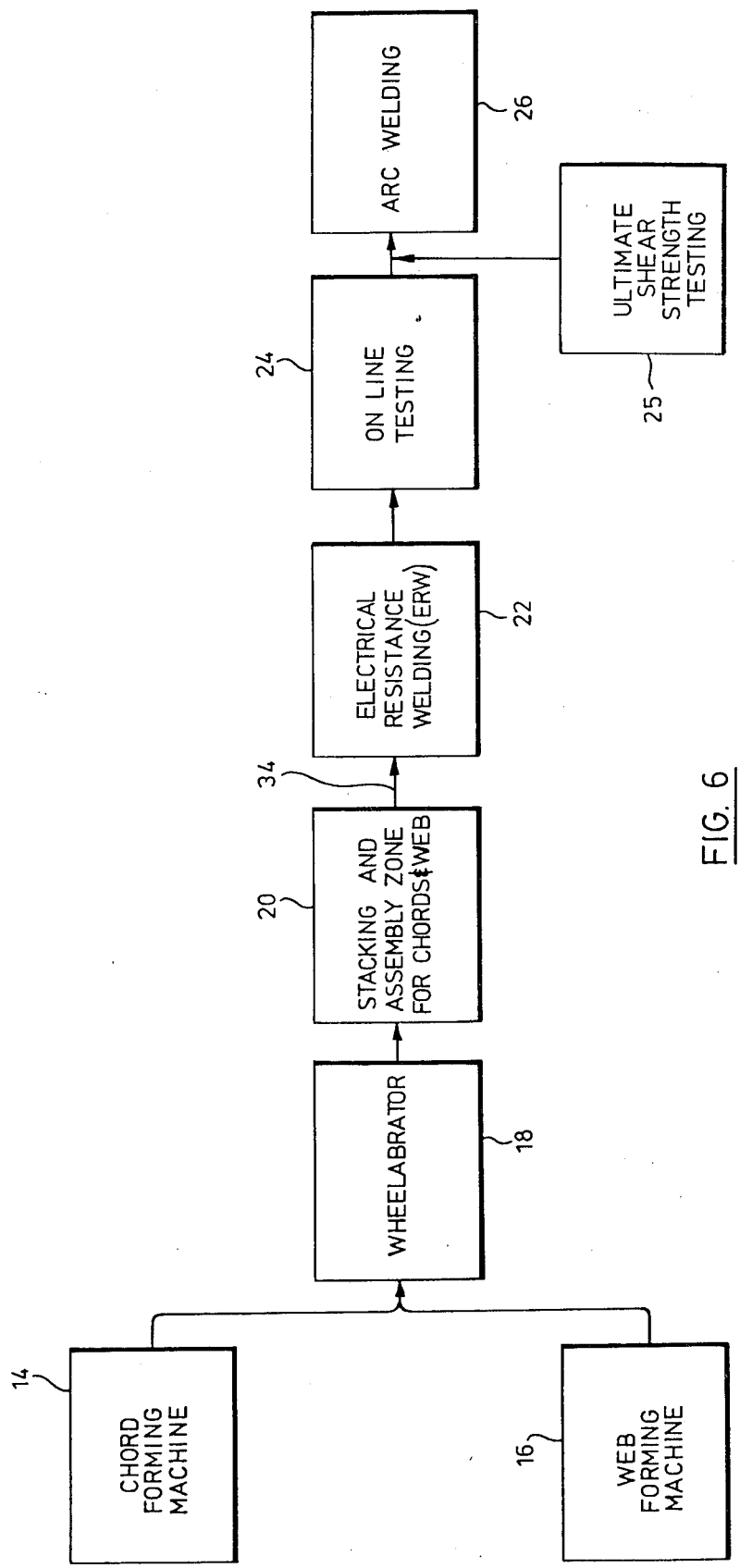
FIG. 6 is a block diagram illustrating the various steps in the fabrication of open web steel joists.

The upper and lower chord members 4 and 6 respectively are formed at a chord forming station having a chord forming machine 14 as depicted in the block diagram of FIG. 6.

The upper and lower chord members 4 and 6 are cold formed in the chord forming machine 14 in a well-known manner whereby flat steel plate or chord forming material is unrolled from a coil, straightened and successively bent by roller dies to impart the cross-sectional configuration area to the chord members 4 and 6 depicted in FIG. 2. The chord members are then cut to length.

FORMATION OF WEBS

The zig-zag web rod 8 is formed at a web forming station having a web forming machine 16 as depicted in the block diagram of FIG. 6.

The web forming machine draws steel rod or web forming material from a coil, descales the oxide coatings of the rod, straightens the rod, cuts the rod to length and then imparts the continuous zig-zag configuration to the web rod 8 by uniformly bending equal sections of the web forming material into an undulating configuration of generally uniform pattern having a series of apices presented by the bent web forming material, all of which is accomplished in a well-known manner.

WHEELABRATOR

Although the chord forming machine 14 and web forming machine 16 are designed to descale the chord members 4 and 6 and the web rod 8, not all of the scale is removed. Under these conditions, excessive sparking occurs at the panel points R or common regions of contact as the chord members 4 and 6 are resistance welded to web rod 8; and the welded joint at the panel points 8 frequently break when a small load is applied to them.

Accordingly, it is important that the cold rolled upper and lower chord members 4 and 6 and web rod 8 be passed through a wheelabrator 18 or a cleaning surface station prior to welding. The wheelabrator removes the loose mill scale from the chord members 4 and 6 and web rod 8 in a manner known to the art.

The wheelabrator 18 leaves the chord members 4 and 6 and web rod 8 virtually free of scale so that when the corresponding surfaces of the chord members 4 and 6 are electrically resistance welded to the web rod 8 a strong clean weld joint at panel points R is produced, with a minimum amount of sparking being produced at the panel point R during welding.

SPECIAL TREATMENT OF CHORDS AND WEBS

The chord members 4 and 6 and web rod 8 are to be left indoors long enough prior to electrical resistance welding to ensure that the temperature of the chords 4 and 6 and web rod 8 is between 40° F. and 90° F. This is necessary in order to minimize the temperature differential between the weld zone and the surrounding metal when the truss elements are welded at the common regions of contact or panel points R.

The time lag between the wheelabration operation and the electrical resistance welding should be short enough to ensure that the chords 4 and 6 and web rod 8 remain relatively free of dirt or oxides prior to welding. This time lag should not be more than 5 days.

STACKING AND ASSEMBLY ZONE FOR CHORDS AND WEBS

Once the chord members 4 and 6, and web rod 8 have been formed in the chord forming machine 14 and web forming machine 16, respectively, and descaled in wheelabrator 18, they are then stacked and assembled prior to being electrically resistance welded as illustrated by the number 20 in the block diagram of FIG. 6.

Figure 7:
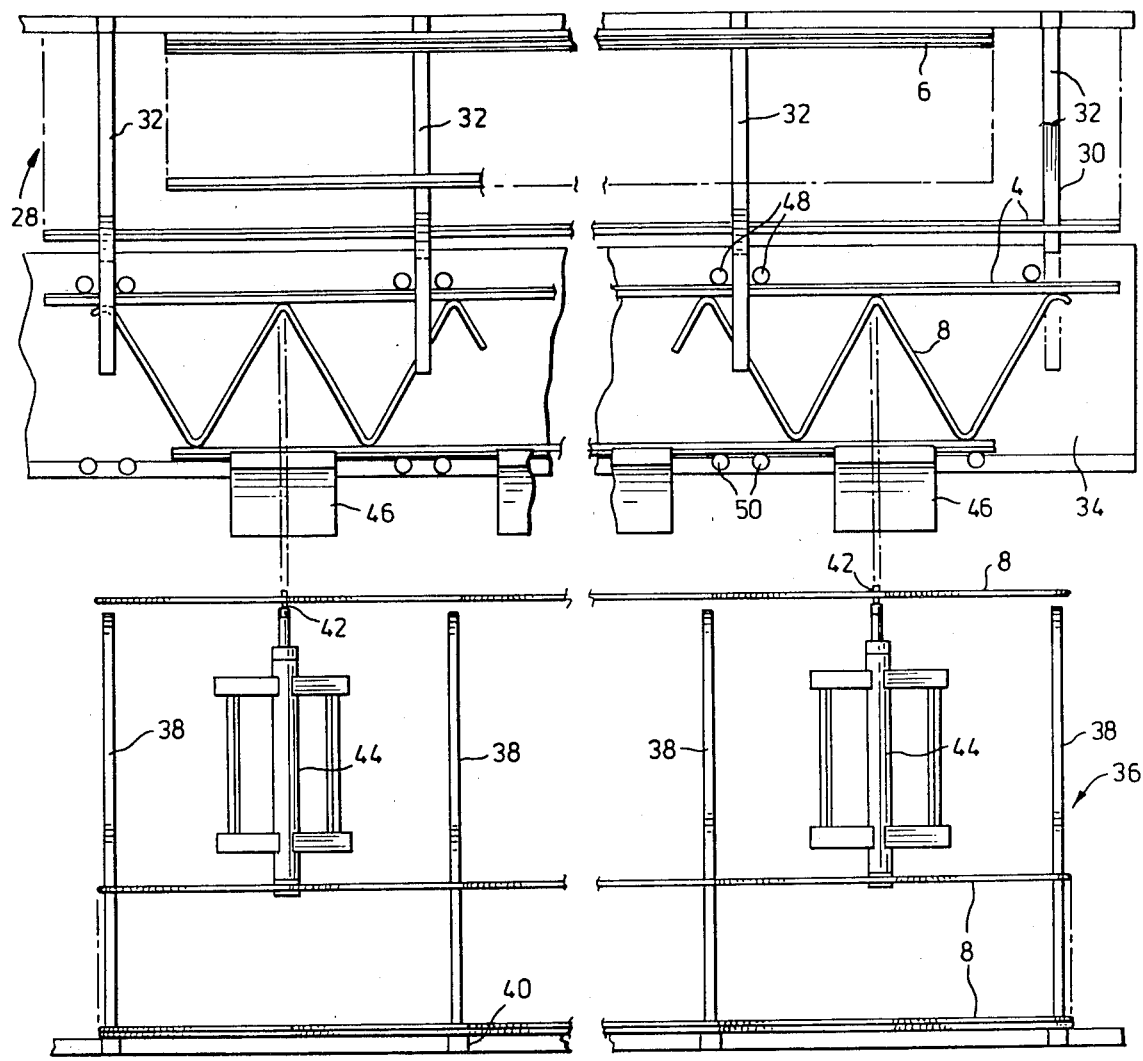
FIG. 7 is a top plan view of the stacking and assembly zone for chords and web.
Figure 8:
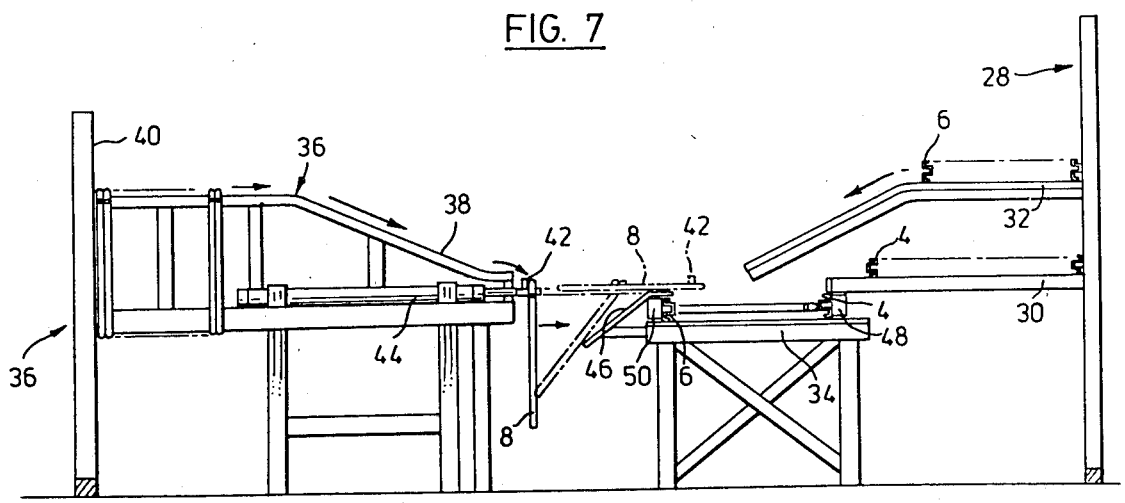
FIG. 8 is a side elevational view of the stacking and assembly zone for chords and web, illustrated in FIG. 7.

Stacking and assembly zone 20 is more particularly depicted in FIGS. 7 and 8 which includes a generally vertical chord stacking structure 28 having cantilevered shelf members 30 and 32. The upper chord members 4 are stacked horizontally on lower shelf members 30, while the lower chord members 6 are stacked horizontally on the upper shelf member 32. The outwardly projecting end of the upper shelf members 32 are declined towards the assembly line 34 (which defines the welding path) in order to facilitate the manual placement of lower chord members 6 onto the assembly line 34.

The undulating or zig-zag web rods 8 are vertically supported on a series of hydraulic web supports 36 which are disposed parallel to one another at right angles to the assembly line 34 as illustrated in FIGS. 7 and 8. The hydraulic web supports 36 include upper horizontal rail member 38 which supports the web rods 8 at the apices of the zig-zag configuration. The horizontal rail member 38 is inclined at one end thereof to facilitate the manual loading of the web rods 8 onto finger 42. The hydraulic web supports are also provided with a stop 40 which prevents the web rods 8 from falling off the hydraulic web supports 36.

The web rods 8 are manually and individually pulled along horizontal rail members 38 onto finger 42. The finger 42 is connected to a hydraulic unit 44, which when activated, causes the finger 42 to travel outwardly toward the assembly line 34 carrying the web rod 8 with it.

As the finger 42 travels toward the assembly line 34 the vertically hanging web rod 8 meets inclined members 46. The inclined members 46 are supported along one edge of assembly line 34 as shown in FIGS. 7 and 8. As the finger 42 passes over the inclined surfaces of members 46 the vertically hanging web rod 8 pivots about finger 42, which swings the web rod 8 to be horizontal disposition on the assembly line 34. The finger 42 releases web rod 8 upon being withdrawn hydraulic unit 44.

The upper chord member 4 is then manually placed on the assembly line 34 so that it is located intermediate the roller guides 48 and web rod 8. The lower chord member 6 is then manually placed on the assembly line 34 so that it is located intermediate the roller guide 50 and web rod 8. The assembly line 34 supports the joist along the welding path defined by the assembly line 34.

The chord members 4 and 6 and web rod 8 are then manually moved to the resistance welding station having electrical resistance welding machine 22, which is illustrated in the block diagram of FIG. 6.

GENERAL ARRANGEMENT OF RESISTANCE WELDERS

The electrical resistance welding machine 22 used in the preferred embodiment is known as the Newcor Ser. No. 2055.

At the electrical resistance welding machine 22 the web rod 8 is manually located relative to the chord members 4 and 6 as illustrated in FIG. 9, such that the assembly is in a web horizontal position. The joist assembly 2 is delivered to the resistance welding machine 22 on a conveyor belt 34 which passes through the center zone of the electrical resistance welding machine 22.

The joist chords 4 and 6 and intermediate web rod 8 are clamped in the first drive clamps 50 and mechanically propelled forwardly, into the electrical resistance welding machine 22 a variable amount to accommodate the initial set up, or an indexed amount established by the distance between panel points R, or the common regions of contact.

The electrical resistance welding machine 22 in the preferred embodiment comprises of four welding heads 51 mounted in pairs on guns A and B. Guns A are located on one side of the conveyor belt 34 while guns B are located on the other side of the conveyor belt 34. The two welding heads 51 on a gun set are mounted 24" apart to match the panel spacing P of the joist 2. Guns B are set 12" downstream of guns A to accommodate the offset between the top chord 4 and the bottom chord 6 panel points R. The distance between the guns A and B perpendicular to the direction of joist travel can be adjusted to allow for variation in the joist depth D.

Each pair of guns is electrically controlled by a welding sequence controller 60, more particularly identified in the trade as a NENA 12 N3H non-synchronous control which shall be described herein. Each pair of guns can be operated independently electrically so that either the upper chord member 4 may be resistance welded to the undulating web rod member 8 at the two panel points R, or the lower chord member 6 may be resistance welded to the undulating web rod 8 at another set of panel points R or common regions of contact. When both pairs of guns A and B are operating, the upper chord member 4 and lower chord member 6 are each electrically resistance welded to the web rod 8 at two common regions of contact. All four guns operate from a common hydraulic source 52 in terms of positioning and pressure associated with welding.

FIG. 10 illustrates the side elevational view of a typical welding head 51.

Each welding head 51 is electrically connected to a 250 KVA single phase water cooled transformer 59. The primary voltage used is 550 volts. The 250 KVA high voltage low amperage of 550 volts is stepped down by the transformer 59 to a low voltage high amperage output. This output or secondary voltage may be selected from a series of eight taps by operating the tap switch 61. There are eight tap settings with secondary voltages increasing uniformly from 6.11 volts at the first tap to 14.85 volts at the eight tap. The secondary voltage outputs corresponding to the eight taps are as follows:

| Tap | Volts |
| --- | --- |
| 1 | 6.11 |
| 2 | 7.36 |
| 3 | 8.61 |
| 4 | 9.86 |
| 5 | 11.10 |
| 6 | 12.35 |
| 7 | 13.60 |
| 8 | 14.85 |

The welding head includes two electrodes 55 and 57 which are adapted to clamp and weld the lower chord member 6 or upper chord member 4 to web rod 8 at the common regions of contact. The electrodes 55 and 57 are normally separated when the electrical resistance welding machine 22 is in the non-welding mode. However, when the resistance welding machine 22 is operating the hydraulic source 52 activates the electrodes 55 and 57 and forces them together so as to clamp and hold upper chord member 4 or lower chord member 6 to web rod 8. Current then passes through the electrodes and the weld zone and electrically resistance welds the chord member 4 or 6 to web rod 8. The hydraulic pressure to the electrodes 55 and 57 is then removed so that the electrodes 55 and 57 clear the chord member 4 or 6 and web rod 8.

Each welding head 51 is adapted to pivot about a shaft 53 in the direction of arrow M so that the welding head is either in the lower horizontal position illustrated in FIG. 10, or in an inclined position such that the electrodes 55 and 57 are located above the joist 2.

The welding heads 51 weld in the horizontal position. The two welding heads 51 on guns A weld the upper chord member 4 to the undulating web rod 8 at two panel points R at the same time that the welding heads 51 on guns B weld the lower chord member 6 to the undulating web rod 8 at another set of panel points R. Once the upper and lower chord members 4 and 6 respectively are welded to rod 8, the welding heads 51 pivot about shaft 53 in the direction of arrow M so that the electrodes 55 and 57 clear the joist 2, and the joist 2 is then indexed along the conveyor belt 34 by the first drive clamp 50, a distance of 48" so that the next panel points can be welded.

The welding, pivoting and indexing action is repeated until the entire length of the joist 2 has been welded at panel points R. The indexing is first accomplished by the action of the first drive clamp 50, and then by the action of the second drive clamp 54 alone.

The joist 2 is guided along the conveyor belt 34 by the first drive clamps 50, second drive clamp 54, and a series of guides 56.

The various steps of welding, pivoting and indexing are controlled by the main operator control panel 58 which activates a series of relays in panel 61 in a manner characteristic of the Newcore Ser. No. 2055 which is well known in the trade.

INDEXING

The indexing action may be best understood by referring to FIG. 9A which illustrates the first drive clamp generally depicted as number 50. The first drive clamp 50 includes pinch rolls 50p and drive rolls 50d which co-act so as to pinch the upper chord member 4. The drive rolls 50d are connected to the hydraulic motor 50m by a shaft 50s. The drive rolls 50d are activated by the hydraulic motor 50m which is connected to the hydraulic power source 52 by conduit 50c. The hydraulic motor 50m causes the drive rolls 50d to rotate in the direction of arrow G which draws or indexes the upper chord member 4 through the electrical resistance welding machine 22 in the direction of arrow H illustrated in FIG. 9.

A first encoder 50e is connected to the drive rolls 50d by shaft 50s. As the drive rolls 50d revolve, the encoder 50e electronically counts the number of revolutions of the drive rolls 50d and emits electronic pulses through an electrical conduit 50w which are received by a positioning controller 140.

The positioning controller 140 includes a digit display counter 142 which shows the number of pulses counted during the indexing of joist 2 through the electrical resistance welding machine 22.

In the preferred embodiment a digit count of 3465 represents that the joist 2 has travelled a distance of 48 inches, or two panel lengths P. Once the digital display counter 142 reaches the count of 3465 the hydraulic fluid from the hydraulic source 52 is no longer supplied to the hydraulic motor 50m; the hydraulic motor 50m stops and the indexing of joist 2 is complete. The positioning controller 140 includes an index thumb wheel switch 144 which is used to preset the distance the joist 2 will index forward in the electrical resistance welding machine 22; in the preferred embodiment the index thumb wheel switch 144 is set at 3465.

In order to ensure that the joist 2 will stop at the indexed position corresponding to the 48 inch distance of travel it is desirable that the joist 2 begin to slow down near the end of its indexed travel. The positioning controller 140 includes a deceleration start switch 146 for this purpose, which is set at 3100.

When the digit display counter 142 reaches the count of 3100 an electrical signal is sent through the electrical conduit 50x to a deceleration hydraulic valve 50v which gradually slows down the supply of hydraulic fluid to the hydraulic motor 50m.

The second drive clamp 54 functions in an identical manner as that of the first drive clamp 50, and includes a second encoder 54e which is electrically connected to the positioning controller 140. A second drive clamp 54 is needed to index the joist 2 through the electrical resistance welding machine when the joist 2 has moved past the first drive clamps 20 yet still in the electrical resistance welding machine 22.

ELECTRODE COMPOSITION

Electrodes usually include a heat exchange means adapted to cool the electrodes during welding; and normally comprises of water flowing through the electrodes.

A key factor in the economics of manufacturing open web steel joists 2 by the multiple impulse welding procedure described herein lies in the utilization of electrodes 55 and 57 having a specified copper composition.

In the preferred embodiment the electrode 55 which comes into contact with either the upper chord member 4 or lower chord member 6 has a relatively higher electrical resistance to the flow of electric current than electrode 57 which comes into contact with the web rod 8. More particularly electrode 55 has a copper beryllium tungsten composition and the electrode 57 has a copper beryllium composition. The electrode 55 used in the preferred embodiment is comprised of copper having a 10 W3 designation which is well known in the trade. The electrode 57 which comes into contact with the web rod 8 is comprised of copper having an RWMA Class 3 composition.

When the 10 W3 and the RWMA Class 3 copper is used in electrodes 55 and 57, respectively the electrodes 55 and 57 last much longer than electrodes manufactured from other materials or copper compositions, and accordingly the multiple impulse resistance welding procedure described herein becomes financially attractive.

It is not known why the electrodes 55 and 57 last longer if they have the composition described. However, it is known that the chord member 4 or 6 has a smaller cross-sectional area than web rod 8 in the common region of contact and therefore the heat generated in the chord member 4 or 6 has a tendency to be conducted away by the electrode 55 by the heat exchange means referred to earlier. It is suspected that the higher resistance of electrode 55 causes the electrode 55 to heat up to a higher temperature than electrode 57 and therefore tends to inhibit the conduction of heat from the chord member 4 or 6 in the common region of contact by setting up a thermal barrier, which increases the efficiency of the welding process.

MULTIPLE IMPULSE ELECTRICAL RESISTANCE WELDING TECHNIQUE

The method for controlling the heat balance in welding materials having dissimilar cross-sectional areas is accomplished by utilizing multiple impulses of electric current which more uniformally heat the dissimilarly thick masses and result in a stronger weld with less discolouration and warpage than found in conventional techniques.

According to the preferred embodiment of this invention the novel method for welding open web steel joists embraces repeated cycles having essentially the following characteristics.

The welding electrodes 55 and 57 are activated by the hydraulic source 52 so as to clamp the chord member 4 or 6 and web rod 8 and exert an extended force on the web rod 8 and upper and lower chord members 4 or 6 respectively along the common regions of contact at panel points R so as to urge chord member 4 or 6 and web rod 8 together at the common region of contact. The web rod 8 and upper or lower chord members 4 or 6 respectively are subjected to the electrode force for a short period of time before the initial application of current to the electrodes. The interval of time between the initial application of the electrode force on the work and the first application of welding current is referred to herein as "squeeze time".

The electrode force is maintained throughout the multiple impulse welding technique.

Once the initial squeeze time has elapsed an impulse of current passes through the electrodes 55 and 57 and the weld zone in the vicinity of the panel points R, which raises the temperature of the weld zone. The time that the current actually flows during any one impulse is referred to herein as the "heat time".

The welding current is interrupted or terminated for a specific "cool time" which represents the interval between the end of one heat time and the start of the next.

A second impulse of current is then applied which further increases the temperature of the material followed by a cool time. This procedure is repeated several times whereby each impulse of electric current raises the temperature of the material uniformly and slowly in stages so as to accomplish correct heat balance. Since the shortest practical time of current flow is utilized in each multiple impulse the escape of generated heat energy from the region of contact is minimized thereby reducing discolouration, warpage and undesirable metallurgical changes in the metal immediately surrounding the nugget. Also the temperature in each member in the common region of contact will be more closely matched, so as to effectively weld the members.

Since the electrode force is maintained during each of the heat time and cool time, each successive interval of heat time in combination with electrode force causes the web rod 8 and the upper and lower chord members 4 and 6 respectfully to fuse or flow and bond with one another along the common regions of contact or panel points R.

After the last impulse of electric current there is "hold time" which represents the time during which the force of electrodes 55 and 57 remains applied, and after which the electrode force is removed.

Once the electrode force is removed the welding heads 51 pivot about shaft 53 so that the electrodes 55 and 57 clear the joist 2. The joist 2 is then indexed along the conveyor belt 34 by the first drive clamp 50, a distance of 48" so that the next set of panel points can be welded, as heretofore described.

In this way the multiple impulse electrical resistance welding technique comprises of a series of time controlled intermittent impulses of electric current.

WELDING SEQUENCE CONTROLLER

Each pair of guns A and B is electrically controlled by a welding sequence controller 60 which utilizes NENA 12 N3H nonsynchronous controls and which also controls the multiple impulse procedure. The welding sequence controller is a component of the Newcor Ser. No. 2055 electrical resistance 60 welding machine 22, which is well known in the trade.

The welding sequence control panel 60 includes seven variable control dials and four switches which control, on a time basis, the various sequences of the multiple impulse resistance welding technique herein described. The time basis is associated with each cycle of an alternating current having a 60-cycle per second power source. For example 300 cycles at 60 cycles per second would correspond to 5 seconds.

The "squeeze" control dial indicated at 62 is a variable control allowing setting of the time interval between the initial application of the electrode force on the work and the first application of welding current. Since this is not crucial to the actual welding, it is normally set at 120 which corresponds to 2 seconds.

The variable "Heat" control dial 64 allows the operator to set and control the interval of time that the current actually flows during any one pulse. A heat time of 27 for example would represent 27 alternating current cycles or the equivalent of 0.45 seconds based on the 60 cycle per second power supply, as shall be described herein the heat time is normally set at 27 for the range of web rod diameters and chord thicknesses covered in Table 2.

The cool time is controlled by the "Cool" control indicated at 66 in FIG. 11, which is the variable control for controlling the interval in cycles between the end of one heat time and the start of the next. In the preferred method, the cool time is normally set at 3 which represents 3 alternating current cycles or the equivalent of 0.05 seconds based on the 60 cycle per second power supply.

The "Hold" variable control dial 68 allows setting of the time interval in cycles during which the electrode force remains applied after the last impulse of current. In the preferred method the hold time is set at 60 cycles or the equivalent of one second.

The "Weld Interval" variable control dial 70 can be used to set the total time interval which includes the squeeze time, all the heat and cool times when making one multiple impulse weld, and the hold time.

The "Off" variable control dial 72 is used to set the length of time in cycles when the electrodes 55 and 57 are off the work prior to the start of the next weld. Since the time required to index the joist forward for the next set of welds actually controls when the next weld can be started the off time has no particular meaning and can be set to a minimum time.

FIG. 12 graphically illustrates the current output from the welding sequence controller 60 during the multiple impulse electrical resistance welding procedure. The magnitude of the current is found on the ordinate axis and the time reference is found on the abscissa axis in FIG. 12.

The graph in FIG. 12 demonstrates that there is no current during the squeeze time when the electrodes 55 and 57 squeeze the work at panel points R. But after a short time interval an impulse of alternating current passes through the electrodes 55 and 57 and the weld zone for a period of time known as the heat time. The resistance of the chords 4 and 6 and the web rod 8 to the current causes the weld zone to heat up. After the first burst of alternating current there is a cooling interval or a cool time when no current is applied. Successive impulses of alternating current are applied and each are followed by a cool time. The final impulse of alternating current is followed by a hold time which is the time interval in cycles during which the electrode force remains applied after the last impulse of current.

Referring again to FIG. 11 the "Percent Heat" variable control dial 74 in conjunction with the tap settings on transformer 51 controls the magnitude of the secondary current used for welding. For example if tap 2 is selected by the tap switch 61 and the "Percent Heat" control dial is set at 50% the secondary voltage corresponding to this setting is (7.364.5) 3.68 volts.

The "High Low" switch 75 is operable to engage the high scale mode or the low scale mode of the "Sequence" control dial 62. Therefore if the high scale mode is engaged with squeeze time would be read from the high scale with corresponding higher squeeze time than if the low scale mode is engaged by the "High Low" switch 76.

The "Repeat Non-repeat" switch 78 is operable to control the number of impulses of secondary current output. In the non-repeat mode only one impulse of alternating secondary current is delivered to the electrodes 55 and 57 and weld zone. In the repeat mode the transformer 51 delivers the programmed number of multiple impulses of alternating current.

The "Spot Pulsation" switch 80 is adapted to put the welding machine 22 into a spot welding mode or a pulsation mode. For the multiple impulse electrical resistance welding technique described herein the "Spot Pulsation" switch 80 would be in the pulsation mode.

The "Weld No Weld" switch 82 will eliminate the secondary current in the no weld mode. The "Weld No Weld" switch 82 allows the operator to have a preliminary run through the welding procedure described herein without welding the work so as to insure that the welding machine 22 is working properly.

PARAMETER SETTINGS FOR WELDING SEQUENCE CONTROLLER

Table 2 tabulates the settings for the control dials on the welding sequence control panel 60 for a range of web rod diameter chord thicknesses and joist steps D found in Table 1.

For example if a 7/8 inch diameter web rod 8 is welded to an upper and lower chord 4 and 6 respectively each having a thickness of 0.200 inches, 750 pounds per square inch of hydraulic pressure is applied to the weld zone by the electrodes 55 and 57. The "Percent Heat" dial 75 would be set at 90% using tap 2; such that the secondary voltage from the transformer 51 would be (0.9×7.36) 6.62 volts. The weld interval would be set for 330 cycles or the equivalent of 5.5 seconds.

As previously mentioned the squeeze time is normally set at 120 cycles or the equivalent of 2 seconds. The heat time is set at 27 cycles or 0.45 seconds and the cool time is set for 3 cycles or 0.05 seconds. Therefore each impulse cycle which includes a heat and cool time lasts for 0.5 seconds.

As described herein the hold time is normally programmed for 60 cycles or the equivalent of 1 second. Since the weld interval equals the squeeze time plus the hold time plus the product of the sum of the heat time and the cool time multiplied by the number of impulses, the number of impulses in the particular example is five.

The parameter settings for various sizes of web rod diameters and chord thicknesses may be obtained from table 1 and 2.

DESCRIPTION OF MAIN OPERATOR CONTROL PANEL 58

Figure 13:
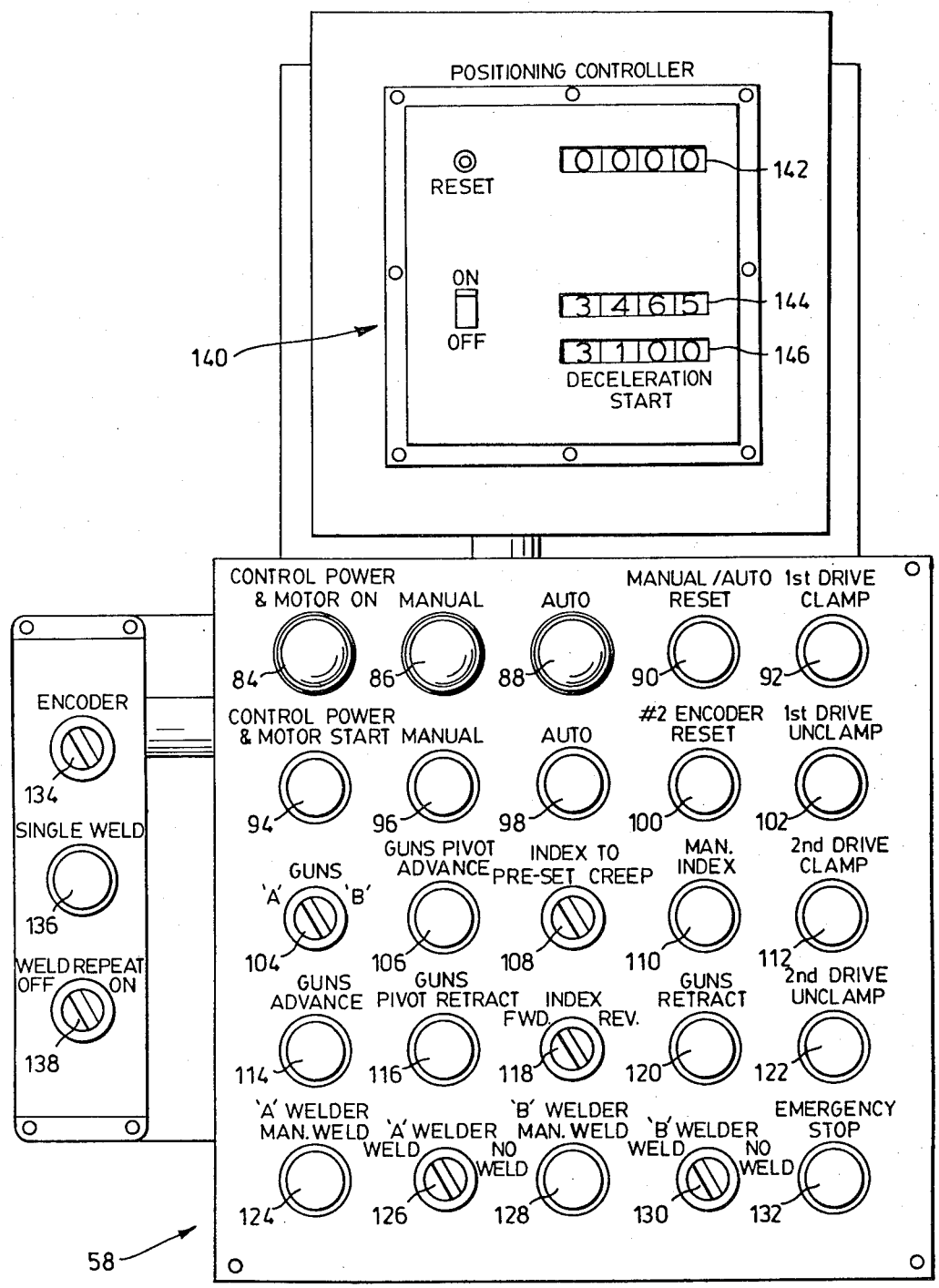
FIG. 13 is a front elevational view of the panel of the operator control.

Although the main operator control panel 58 is an intrical part of the Newcor Ser. No. 2055 resistance welding machine 22 which is common to the trade, the function for each of the stations on the main operator control panel 58 depicted in FIG. 13 shall be described. The "Control Power & Motor On" pilot light 84 indicates that the control power is on and is activated by a push button 94.

The "Manual" pilot light 86 is adapted to indicate that the machine is ready for operation in the manual mode and is activated by push button 96 when operating in a manual mode or by push button 90 followed by push button 96 when switching from automatic mode to manual mode.

The "Auto" pilot light 88 indicates that the electrical resistance welding machine 22 is ready for operation in an automatic mode and is activated by push button 98 when operating in the automatic mode or by pressing push button 90 followed by push button 98 when changing from the manual mode to the automatic mode.

The "Manual/Auto Reset" push button 90 prepares the electrical resistance welding machine 22 for switching welding machine 22 from manual and automatic modes of operation and is followed by pushing either the "Manual" push button 96 or "Auto" push button 98.

The "First Drive Clamp" push button 92 is operable to clamp the upper and lower chord members 4 and 6 respectively of the joist 2 by using pinch rollers 50p in the first drive clamps 50 so that the joist 2 can be driven by the drive rolls 50d, into the electrical resistance welding machine 22.

The "Control Power & Motor Start" push button 94 is operable to turn on the electrical control power to the electrical resistance welding machine 22 and also starts the hydraulic power source 52.

The "Manual" push button 96 sets the electrical resistance welding machine 22 to operate in the manual mode.

The "Auto" push button 98 is operable to set the electrical resistance welding machine 22 to operate in an automatic mode.

The "No. 2 Encoder Reset" push button 100 is adapted to reset the second encoder 54e associated with the second drive clamp 54 to 0 which signal recognizes that the joist 2 has been positioned readily for indexing.

The "First Drive Unclamp" push button 102 is operable to cause the pinch rolls 50p and drive rolls 50d in the first drive clamps 50 to separate and therefore freeing the joist 2.

The "Guns A B" selector switch 104 allows the operator to determine which pair of guns will fire when operating in the manual mode.

The "Guns Pivot Advance" push button 106 is operable to cause both guns A and B to pivot forward in the position shown in FIG. 10 ready for welding.

The "Index to Preset Creep" selector switch 108 is adapted to advance the joist 2 to a preset distance established by the encoder when said switch is in the index to present mode. The present distance is normally the amount required to index the joist 2 a fixed multiple of panel point lenghts P. When the "Index To Preset Creep" selector switch 108 is in the creep mode the joist 2 moves forward at a very slow pace through the electrical resistance welding machine 22 and does not stop at any preset index point.

The "Manual Index" push button 110 is operable to cause the joist 2 to move through the electrical resistance welding machine 22 when operating in the manual mode. The joist will either advance a preset amount or will creep along depending upon the position of the "Index to Preset Creep" selector switch 108.

The "Second Drive Clamp" push button 112 is adapted to clamp the upper and lower chord members 4 and 6 respectively of the joist 2 when using the second set of drive clamps 54 and is similar in operation to the "First Drive Clamp" push button 92.

The "Guns Advance" push button 114 is operable to cause the electrodes 55 and 57 in the welding heads 51 to advance towards each other making contact across a panel point R in the joist 2 through the web and chord section.

The "Guns Pivot Retract" push button 116 is adapted to cause the welding guns A and B to pivot in the direction of arrow M in FIG. 10 so that the electrodes 55 and 57 are away from the joist.

The "Index Forward/Reverse" selector switch 118 is used in conjunction with the "Manual Index" push button 110 and the "Index to Preset Creep" selector switch 108 to indicate the direction which the joist 2 should move through electrical resistance welding maching 22.

The "Guns Retract" push button 120 is operable to cause the electrodes 55 and 57 in the welding head 51 to retract away from each other into the position shown in FIG. 10.

The "Second Drive Unclamp" push button 122 is used to cause the second drive clamps 54 to move away from each other thereby freeing the joist 2.

The "A Welder Manual Weld" push button 124 is used to activate the gun set A to weld in the manual mode.

The "A Welder Weld No Weld" selector switch 126 is operable such that all sequences associated with guns A will activate yet the guns A may or may not weld depending on the switch position.

The "B Welder Manual Weld" push button 128 is used to activate guns B in the manual mode.

The "B Welder Weld No Weld" selector switch 130 is operable such that all sequences associated with guns B will activate yet the guns B may or may not weld depending on the switch position.

The "Emergency Stop" 132 is used to shut down all functions of the electrical resistance welding machine 22 immediately.

The "Encoder No. 1 No. 2" selector switch 134 is operable to cause the response from either the first encoder 50e or the second encoder 54e to be displayed on the positioning controller 140.

When the "Single Weld" selector switch 136 is in the off position a single weld in the automatic mode will be activated by this push button.

The "Weld Repeat Off On" selector switch 138 is operable to cause the electrical resistance welding machine 22 to operate in the automatic mode but will either limit the number of welds to one in the off mode or allow continuous automatic welding in the on position.

The "Positioning Controller" 140 indicates the distance travelled by the joist. The counter 142 at the top of the "Positioning Controller 140" shows the number of pulses that the encoder selected by "Encoder No. 1 No. 2" selector switch 134 has registered during the movement of the joist 2 through the electrical resistance welding machine 22. The index thumb wheel 144 switch determines the total indexing distance for the encoder to preset the distance the joist 2 will move forward in the electrical resistance welding machine 22. The index thumb wheel 144 reflects the distance associated with the "Index to Preset" position on selector switch 108. The deceleration start thumb wheel 146 determines the portion of the preset index distance where the joist 2 will begin to slow down in order to stop at the indexed position.

OPERATING SEQUENCE

Before activating the electrical resistance welding machine 22 to weld the joists 2, the welding sequence controller 60 must be preset to the appropriate weld interval, sequence time, heat time, cool time, hold time and percentage heat as herein before described. The appropriate tap is selected by utilizing the tap switch 61.

The hydraulic pressure is then selected as outlined in table 2. Tables 1 and 2 outline the settings utilized in the preferred method for a range of web rod diameters and chord thicknesses. However it should be understood that they are not the only settings which can be used in association with the multiple-impulse electrical resistance welding technique.

The index on the positioning controller 140 on the operator control panel 58 is then set by programming the index thumb wheel switch 144 and the deceleration start switch 146 which operation establishes the specific distance associated with indexing of the welds automatically.

The electrical resistance welding machine 22 is turned on by pushing the "Control Power and Motor Start" push button 94 and then "Manual" push button 96 to set the machine 22 in a manual mode.

The web rod 8 is then located in the proper position relative to the upper chord member 4 and lower chord member 6, and then the ends of each chord member 4 and 6 respectively adjacent to the guns A are checked to ensure that they are in the required position. The joist 2 is then manually moved past the first drive clamp 50 and the "First Drive Clamp" push button 92 is used to clamp the joist 2 in position. The "Second Drive Unclamp" push button 122 must be energized to make sure the second drive clamp 54 is unclamped for otherwise the machine 22 will not operate.

With "Index Forward/Reverse" selector switch 118 in the forward position the operator brings the joist 2 into the welding machine 22 using the "Index to Preset Creep" selector switch 108 in the creep mode and the "Manual Index" push button 110 until the first set of panel points R on the upper chord member 4 are opposite their respective welding heads 51 on guns A.

At this point the "Guns Pivot Advance" push button 106 is activated which causes guns A and guns B to pivot forward into the horizontal welding position. The "Guns Advance" push button 114 is activated which causes the electrodes 55 and 57 to advance toward each other thereby squeezing the upper chord member 4 and web rod 8. The "Guns A" selector switch 104 is set for guns A and then the "A Welder Manual Weld" push button 124 is activated which causes the welding heads 51 on guns A to weld the upper chord member 4 to the web rod 8 at panel points R.

When "Guns Retract" push button 120 is pushed the guns A and guns B retract from the joist 2. At this stage "Guns Pivot Retract" push button 116 is activated which causes guns A and guns B to pivot upwardly freeing the joist 2 for indexing.

The joist 2 is moved forward in the electrical resistance welding machine 22 into the second welding position by repeating the sequence described above, namely; by selecting the creep mode on the selector switch 108, pushing the "Manual Index" push button 110, and then selecting the forward mode on the "Index Forward/Reverse" selector switch 118. The joist 2 is located such that a second set of panel points R on the upper chord member 4 will be opposite their respective welding heads 51 on guns A, and the first set of panel points on the lower chord member 6 will be opposite their respective welding heads 51 on guns B. The joist 2 will have probably progressed sufficiently into the electrical resistance welding machine 22 to allow the second drive clamp 54 to be engaged by the "Second Drive Clamp" push button 112.

The welding machine 22 is now capable of operating in an automatic mode; and this is accomplished by pushing the "Manual/Auto Reset" push button 90 and then the "Auto" push button 98. The "No. 2 Encoder Reset" push button 100 is activated to reset the second encoder 54e at the starting position to ensure that the first indexing starts from 0000.

When the "Weld Repeat Off On" selector switch 138 is in the off position the operator activates two safety buttons adjacent the welding 22 (not shown) and then pushes "Single Weld" push button 136 causing the welding machine 22 to automatically make a single multiple impulse weld. If all systems appear operational the "Weld Repeat Off On" selector switch 138 can be set for the on position causing the welding machine 22 to automatically continue to index and weld the joist 2 throughout its length.

ON-LINE SHEAR TESTING MACHINE

Periodically one of the welded joists 2 is manually pulled along the conveyor line 34 into the on-line shear testing machine 24 which is located at the end of the conveyor belt 34 as illustrated in FIG. 6. The on-line shear testing machine 24 measures the shear strength of the weld.

Figure 14:
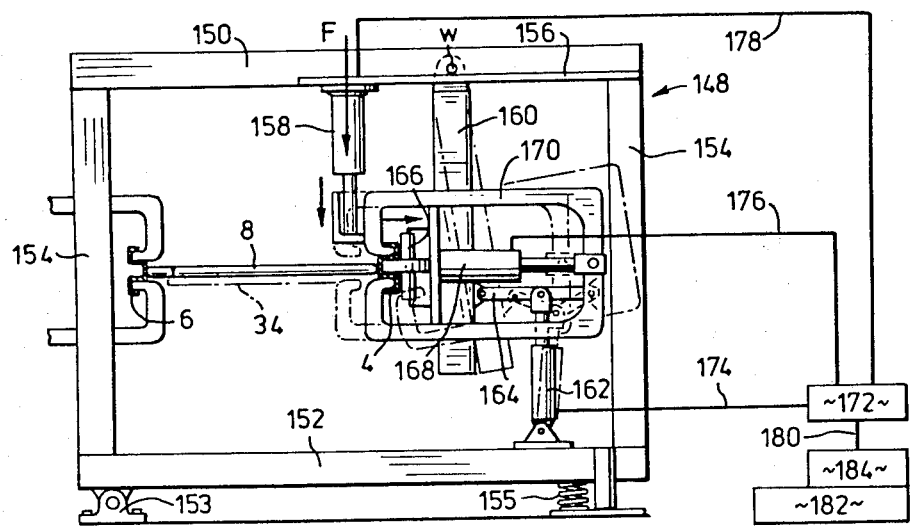
FIG. 14 is a side elevational view illustrating the on line shear testing machine.
Figure 15:
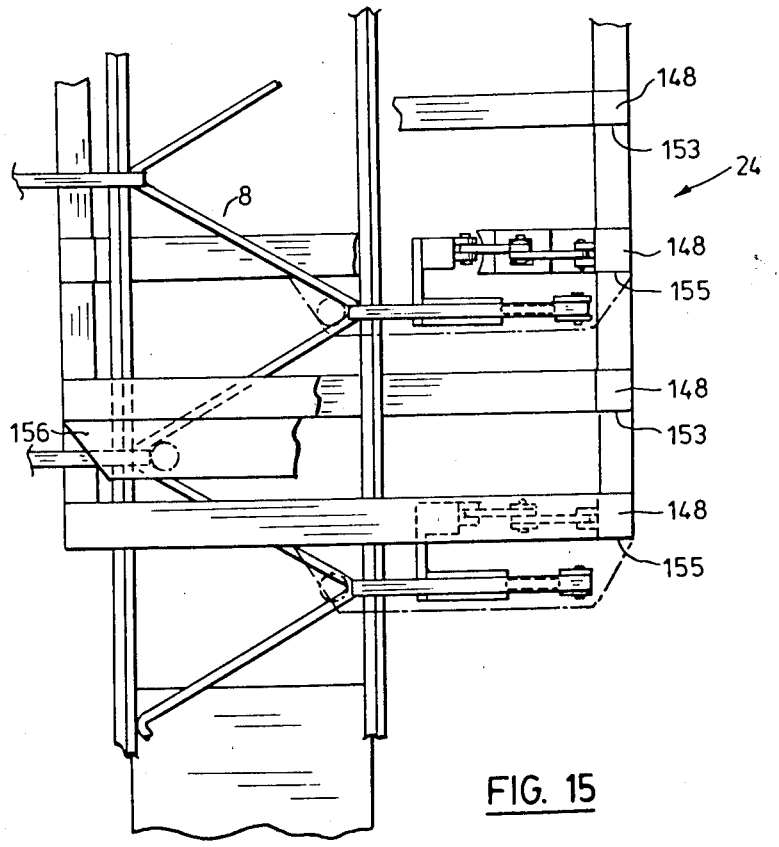
FIG. 15 is a top plan view of the on line shear testing machine of FIG. 14.

The on-line shear testing machine 24 is more particularly shown in FIGS. 14 and 15 and has been designed to simulate the actual loading conditions whereby a lateral force F of 1.65 times the design shear load is applied to the web rod 8 while the chord member 4 and 6 are held in position. The lateral force F is applied simultaneously to the apices of the welded web rod 8 at four points, two of which are adjacent the upper chord member 4 and the other two of which are adjacent the lower chord member 6 as illustrated in FIG. 15.

The on-line shear testing machine 24 includes four generally parallel frames 148 each of which have a generally quadrilateral configuration as illustrated in FIG. 14. Each frame 148 has a top frame member 150, bottom frame member 152 and two side frame members 154.

The top frame member 150 includes an upper plate member 156 which supports hydraulic cylinder 158 and depending arm member 160. The upper portion of the depending arm member 160 is adapted to pivot about point w as illustrated by the hidden lines in FIG. 14.

The lower portion of the depending arm member 160 is connected to a hydraulic cylinder 162 by means of an elbow joint 164 which is also connected to side frame member 154. The hydraulic cylinder is activated by the hydraulic pressure from a hydraulic source 182 which is transmitted through conduits 180 and 174. When the hydraulic cylinder 162 is activated the elbow joint 164 assumes a horizontal position and the depending arm member 160 is formed into a substantially vertical position as illustrated in FIG. 14. When the hydraulic cylinder 162 is deactivated the elbow joint assumes a generally "Y" shaped configuration illustrated by the hidden lines in FIG. 15, which action pulls the depending arm member 160 into the position represented by the hidden lines in FIG. 14.

The depending arm member 160 includes roller 166 which facilitates location of upper chord member 4.

The depending arm member 156 also includes a hydraulic cylinder 168 which is connected to a finger clamp 170. The hydraulic cylinder is also activated by hydraulic pressure from the hydraulic source 182 which is transmitted to conduits 180 and 176. When the hydraulic cylinder 168 is activated the finger clamp 170 is forced into the position illustrated in FIG. 14; and when the hydraulic cylinder 168 is deactivated the finger clamp 170 returns to the position illustrated by the hidden lines in FIG. 14.

The hydraulic cylinder 162 and 168 are deactivated when manually loading the joist 2 into the on-line shear testing machine 24 so that the depending arm member 160 and finger clamp 170 are in the position illustrated by the hidden lines in FIG. 14. Once the joist 2 is located onto the on-line shear testing machine 24 the hydraulic cylinders 162 and 168 are activated by the hydraulic pressure from the hydraulic source 182 and the joist 2 is clamped against the roller 166 by the finger claim 170.

Then the hydraulic cylinder 158 is activated by the hydraulic pressure from the hydraulic source 182 which is transmitted through conduits 180 and 178. The hydraulic cylinder 158 exerts a force F to the web rod 8 at panel point R.

A pressure squeezing valve 172 insures that the joist 2 is clamped into position before the force F is applied perpendicularly against the web rod 8. Table 1 tabulates the value of the design shear load times 1.65 at the resistance welded joint connection. The design shear load is obtained by recognizing the fact that the design shear load is governed by the buckling of the compression diagonal, that is the diagonal length of the web and the web rod dimensions in a manner well known to the trade.

An electric timer 184 activates the hydraulic source 182 for a minimum of five seconds, thereby providing a lateral force F for a minimum of five seconds and is then released. This electric timer 184 can be adjusted to increase or decrease the pressure time. The on-line shear testing machine 24 is non-destructive and successful if no permanent deformation is developed.

Each of said bottom frame members 152 include a pivot 153 and a spring 155 at either ends of said bottom frame member 154 as illustrated in FIG. 14.

The pivot 153 and spring 155 support the frame member 148.

Since it is probable that not all of the welded joints between the web rod 8 and chord members 4 or 6 lie precisely in the same plane when the joist 2 enters the on-line shear testing machine 22. In a web horizontal position, the pivot 153 and spring 155 in each of the frame members 148 are adapted to allow each individual frame member to automatically adjust to the positioning of said welded joint prior to the application of the lateral force F. This action substantially eliminates any inherent stresses that may be caused when the weld joints are not all precisely in the same plane; otherwise the joist 2 would have a tendency to twist under the simultaneous application of the lateral force F to the four points of application.

The preferred on-line shear testing machine 22 simultaneously tests four welded joints, although it is possible to construct the on-line shear testing machine 24 to test any number of weld joints.

Since the on-line shear testing machine is located at the end of the conveyor belt 34 it provides a relatively quick and simple procedure for measuring the shear strength of four welds simultaneously.

ULTIMATE SHEAR STRENGTH TESTING MACHINE

The ultimate shear strength of the welded joist 2 are periodically tested so as to achieve failure loads exceeding the value of the design shear load times 2.5 as tabulated in table 1.

Figure 16:
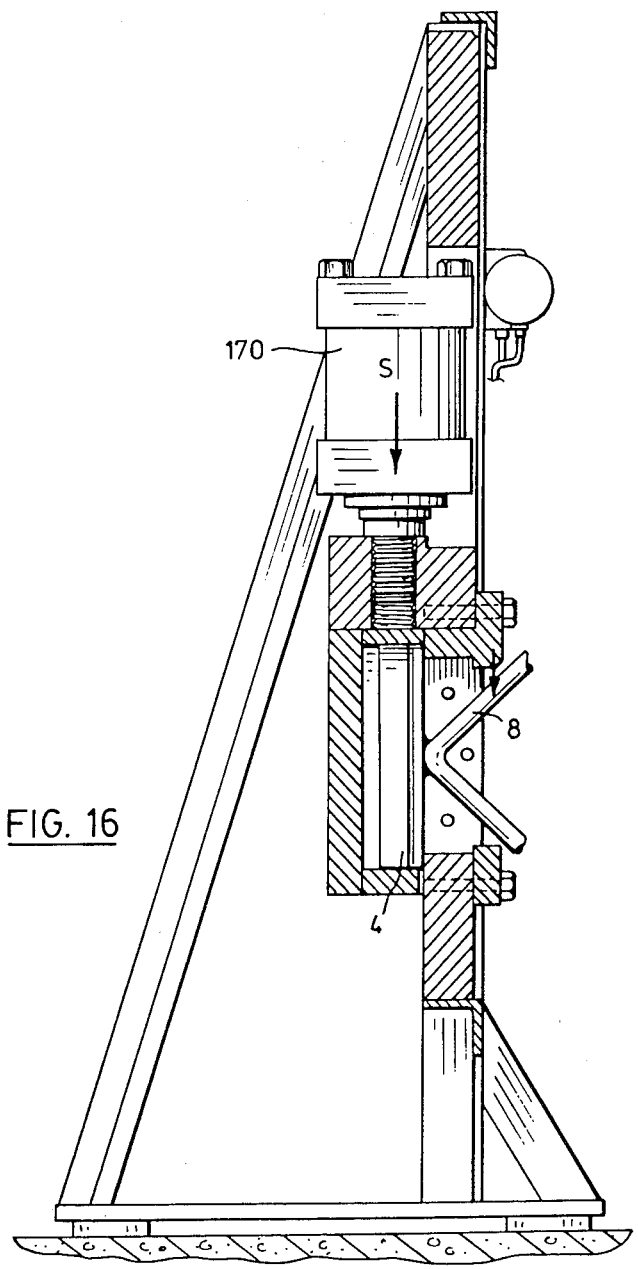
FIG. 16 is a side elevational cross-sectional view of the shear strength testing machine.

This test is done on an ultimate shear strength testing machine 25 designed by the Ontario Research Foundation and is illustrated in FIG. 16.

The web 8 and the chord 4 are cut about three inches from the weld joint to facilitate loading in the testing machine as illustrated in FIG. 16.

The ultimate shear strength testing machine 25 simulates actual load conditions by applying an actual shear force S to the chord 4 while the web 8 is firmly held in position. The actual shear force S is continuously increased until failure occurs. The failure load is measured on the pressure gauge (not shown) and is the ultimate shear strength of the weld connection. The ultimate shear strength varies according to the chord 4 and web rod 8 material and geometry. The load is applied by a hydraulic cylinder 170 which is operated by an electric motor (not shown).

What I claim is:

1. Apparatus for fabricating an open web metal truss derived from substantially uniformly spaced-apart chord members of selected suitable configuration joined by electrical resistance welding to a web member of a substantially uniformly undulating selected suitable configuration along substantially uniformly separated regions of contact established by the apices of said undulating web member, and wherein the cross-section of the web member at the regions of contact exceed the cross-sections of the respective chord members including,
   (a) means for forming chord members from lengths of metal stripping into a selected suitable configuration;
   (b) means for forming web members from lengths of metal wires into a selected suitable configuration;
   (c) treating means for removing scale and surface coatings from each chord and web member so formed;
   (d) means for assembling treated chord and web members into truss defining relation and supporting same in such disposition;
   (e) means for delivering such assembled and supported chord and web members in truss defining relation along a linear path to a welding station;
   (f) at least four electrical resistance welding means located at said welding station in spaced relation to said linear path and to each other, each said welding means including opposed first and second electrode means of selected unequal resistance, each said welding means being operable to simultaneously grip, weld and release such assembled and supported chord members and web members in truss defining relation at one of four juxtaposed regions of contact therebetween, the electrode of higher resistance of each said welding means being disposed so as to contact the chord member and the electrode of lower resistance being disposed so as to contact the web member;
   (g) means for supplying said electrode means while in gripping contact with the chords and web member respectively with a series of time controlled intermittent impulse of heat generating electrical energy sufficient to incrementally raise the members to fusion temperature along the regions of contact; and, (h) means for indexing said delivery means such that at least four juxtaposed regions of contact between the chord members and web member are successively presented to said welding means.

2. Apparatus as claimed in claim 1 wherein said means for forming the chord members includes means for drawing and shaping lengths of metal stripping to impart the requisite cross-section thereto and means for cutting said drawn and shaped metal stripping into selected lengths.

3. Apparatus as claimed in claim 1 or 2 wherein means for forming the said web members includes means for cutting a selected length of metal wire and means for bending same into a substantially uniformly undulating configuration to present a series of uniformly spaced-apart apices.

4. Apparatus as claimed in claims 1 or 2 wherein said treating means includes means for abrading the chord and web members so formed whereby scale and surface coating are sufficiently removed so as to minimize sparking at said regions of contact during the supply of electrical energy to said electrodes.

* * * * *